(12) United States Patent
Pickerd

(10) Patent No.: US 9,599,639 B2
(45) Date of Patent: Mar. 21, 2017

(54) DEVICE AND METHOD TO PREVENT INTER-SYSTEM INTERFERENCE

(71) Applicant: Tektronix, Inc., Beaverton, OR (US)

(72) Inventor: John J. Pickerd, Hillsboro, OR (US)

(73) Assignee: Tektronix, Inc., Beaverton, OR (US)

( * ) Notice: Subject to any disclaimer, the term of this patent is extended or adjusted under 35 U.S.C. 154(b) by 38 days.

(21) Appl. No.: 14/079,801

(22) Filed: Nov. 14, 2013

(65) Prior Publication Data

US 2014/0300371 A1 Oct. 9, 2014

Related U.S. Application Data

(60) Provisional application No. 61/808,746, filed on Apr. 5, 2013.

(51) Int. Cl.

| | | |
|---|---|---|
| *G01R 31/02* | (2006.01) | |
| *G01R 13/02* | (2006.01) | |
| *G01N 31/02* | (2006.01) | |
| *G01N 27/42* | (2006.01) | |
| *F02P 17/00* | (2006.01) | |
| *G01R 31/24* | (2006.01) | |
| *G01R 27/30* | (2006.01) | |

(Continued)

(52) U.S. Cl.
CPC ............ *G01R 13/02* (2013.01); *F02P 17/00* (2013.01); *G01N 27/42* (2013.01); *G01N 31/02* (2013.01); *G01R 13/0236* (2013.01); *G01R 27/30* (2013.01); *G01R 31/24* (2013.01); *G01R 31/2635* (2013.01); *G01R 31/44* (2013.01)

(58) Field of Classification Search
CPC .... G01R 13/02; G01R 27/30; G01R 13/0236; G01R 31/00; G01R 31/002; G01R 31/24; G01R 31/2635; G01R 31/44; G01N 27/42; G01N 31/02; F02P 17/00; H05B 37/03
USPC ......... 324/537, 71, 378, 403, 415, 425, 500, 324/76.11, 76.12, 600, 629, 637, 638; 702/1, 57, 66, 67, 70, 71, 73, 108, 125, 702/127, 182, 183, 189, 190
See application file for complete search history.

(56) References Cited

U.S. PATENT DOCUMENTS 7,642,940 B1 * 1/2010 McKenna et al. ............ 341/120
8,023,573 B2 * 9/2011 Kikuchi ........................ 375/259
(Continued)

FOREIGN PATENT DOCUMENTS

JP 2009236765 A 10/2009

OTHER PUBLICATIONS

Application Brief LAB-WM778, which is titled Using LeCroy's EyeDoctorTM II, Mar. 11, 2009, pp. 1-5.*
(Continued)

*Primary Examiner* — Huy Q Phan
*Assistant Examiner* — Raul Rios Russo
(74) *Attorney, Agent, or Firm* — Michael A. Nelson; Kevin D. Dothager; Marger Johnson

(57) ABSTRACT

A method of preventing inter-system interference while acquiring waveforms in a test and measurement instrument with variation in a device under test system S-parameters. The method includes receiving a waveform from a device under test at the test and measurement instrument, digitizing the waveform, identifying portions of the digitized waveform with different S-parameter characteristics, separating the identified portions of the digitized waveform into different waveforms, and displaying the different waveforms to a user.

16 Claims, 5 Drawing Sheets

(51) Int. Cl.
    *G01R 31/00*     (2006.01)
    *G01R 31/44*     (2006.01)
    *G01R 31/26*     (2014.01)

(56) References Cited

U.S. PATENT DOCUMENTS

| | | | |
|---|---|---|---|
| 8,514,919 B2* | 8/2013 | Estrada et al. | 375/224 |
| 2004/0213417 A1* | 10/2004 | Gessert | H04R 29/005 |
| | | | 381/66 |
| 2005/0131974 A1 | 6/2005 | Letts et al. | |
| 2006/0198431 A1* | 9/2006 | Turpin et al. | 375/224 |
| 2007/0271067 A1* | 11/2007 | Cohn et al. | 702/183 |
| 2007/0273694 A1* | 11/2007 | Dobyns et al. | 345/440.1 |
| 2007/0297537 A1* | 12/2007 | Luce | H04L 27/0014 |
| | | | 375/322 |
| 2008/0126903 A1* | 5/2008 | Wegener | G01R 31/31921 |
| | | | 714/742 |
| 2008/0147342 A1 | 6/2008 | Heuser et al. | |
| 2008/0243406 A1 | 10/2008 | Pupalaikis | |
| 2011/0254721 A1* | 10/2011 | Sakai | H03M 1/1042 |
| | | | 341/147 |
| 2013/0080105 A1* | 3/2013 | Carlson | G01R 31/2841 |
| | | | 702/104 |
| 2013/0096881 A1* | 4/2013 | Jauriqui | G01N 29/043 |
| | | | 702/189 |
| 2013/0332101 A1* | 12/2013 | Pickerd | H04B 3/46 |
| | | | 702/119 |
| 2013/0343442 A1* | 12/2013 | Tan et al. | 375/224 |

OTHER PUBLICATIONS

Extended European Search Report for European Patent Application No. 14163527.6, Feb. 2, 2015, 7 pages, Berlin.

\* cited by examiner

DEVICE AND METHOD TO PREVENT INTER-SYSTEM INTERFERENCE

CROSS-REFERENCE TO RELATED APPLICATION

This application claims the benefit of the filing date of U.S. Provisional Patent Application No. 61/808,746, which is titled "Method to Prevent Inter-System Interference" and was filed on Apr. 5, 2013, the disclosure of which is hereby incorporated by reference herein in its entirety.

TECHNICAL FIELD

This disclosure relates to a method and device for separating and processing long record waveforms that contain segments with variation in the device under test system S-parameters.

BACKGROUND

There are a number of applications currently running on test and measurement instruments, such as oscilloscopes, that process long data records from various serial data links, memory buses such as double data rate (DDR) buses, or multiple mode busses such as a mobile industry processor interface (MIPI). Some of these devices under test (DUT) have modes of transmission where the source or load impedance may be different while the oscilloscope is acquiring the data record. Or, there are DUTs where different transmitters may be connected to a bus at different times during acquisition of data.

An example is a MIPI bus used for camera data in a cell phone. The MIPI bus has a high-speed low-voltage transmitter for moving the camera data, and also has a low-speed high-voltage low power transmitter for signaling. The high-speed low-voltage transmitter has a 50 ohm source impedance, while the low-speed high-voltage transmitter has a source impedance that can vary from 110 ohms and higher. Another example is a bi-directional bus used in memories. With this type of bus, a central processing unit (CPU) transmitter drives the bus during a write operation and the memory chip transmitter drives the bus during a read operation.

Finally, an extreme example is a DDR memory where the write operations have an on-die termination (ODT) turned on during a write, but the ODT is turned off during a read to conserve power. Switching while acquiring the waveform results in severe ringing during the read operation due to the impedance mismatch on the DDR memory.

Current oscilloscope acquisition systems have bandwidth enhance filters and de-embedding and simulation filters with lengths that may span across events in the data record that were obtained under different DUT physical characteristics. The problem observed is convolution of the scope digital signal processing (DSP) filter with the acquisition in combining data from two different system characteristics in a single waveform acquired. Convolution results in the data from a write operation, for example, affecting the data from a read operation out of the filter, and vice versa. Convolution could have an adverse impact on jitter measurements and other measurements. Filters are good for use with time-invariant systems; however, the above described systems are time variant systems that have characteristics that vary between different states in different parts of the acquired time record.

Further, combining two different systems characteristics into a filter convolution will result in erroneous results when using de-embedding or simulation filters generated from applications like serial data link analysis (SDLA). Since the DUT has characteristics that vary over time, a solution is needed to be able to separate and process the different segments with variations in DUT S-parameters.

SUMMARY

Certain embodiments of the disclosed technology include a test and measurement instrument including a receiver structured to receive a waveform from a device under test, a digitizer structured to digitize the waveform and a processor configured to identify portions of the digitized waveform with different S-parameter characteristics, and to separate the identified portions of the digitized waveform into different waveforms. The test and measurement instrument also includes a display to display the different waveforms to a user.

Certain other embodiments of the disclosed technology include a method of preventing inter-system interference while acquiring waveforms in a test and measurement instrument with variation in a device under test system S-parameters. The method includes receiving a waveform from a device under test at the test and measurement instrument, digitizing the waveform, identifying portions of the digitized waveform with different S-parameter characteristics, separating the identified portions of the digitized waveform into different waveforms, and displaying the different waveforms to a user.

Certain other embodiments of the disclosed technology include a test and measurement instrument including means for receiving a waveform from a device under test, means for digitizing the waveform, means for identifying portions of the digitized waveform with different S-parameter characteristics, means for separating the identified portions of the digitized waveform into different waveforms, and means for displaying the different waveforms to a user.

DETAILED DESCRIPTION

Figure 1:
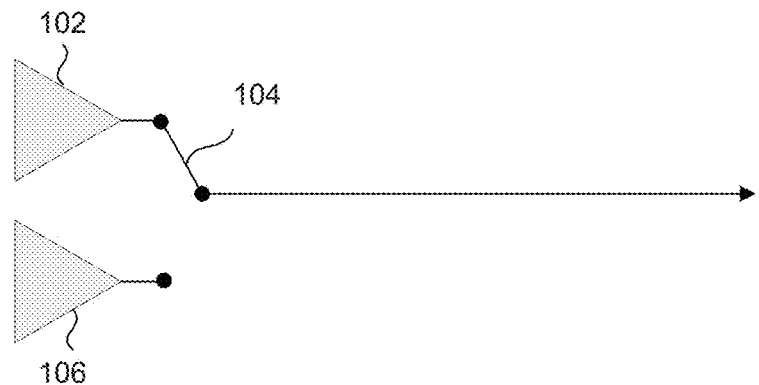
FIG. 1 illustrates two transmitters that may drive a bus of a DUT at different times.

In the drawings, which are not necessarily to scale, like or corresponding elements of the disclosed systems and methods are denoted by the same reference numerals.

FIG. 1 shows two transmitters in a DUT. The first transmitter 102 drives a line for a period of time and then a switch or multiplexer 104 changes so that the second transmitter 106 is driving the line for a period of time. The first transmitter 102 and the second transmitter 106 have different characteristic S-parameters to define their behavior. For example, if the first and second transmitters 102 and 106 were used in a DDR memory, first transmitter 102 would drive the line with ODT turned off. After the switch 104 changes, the second transmitter 106 would drive the link with ODT turned on.

A waveform acquired from a DUT with the two transmitters shown in FIG. 1 has characteristics that changes as a function of time throughout the waveform record due to the change in the DUT hardware configurations during acquisition. The system changes are not continuous, but rather are switched at different points in the record.

Figure 2:
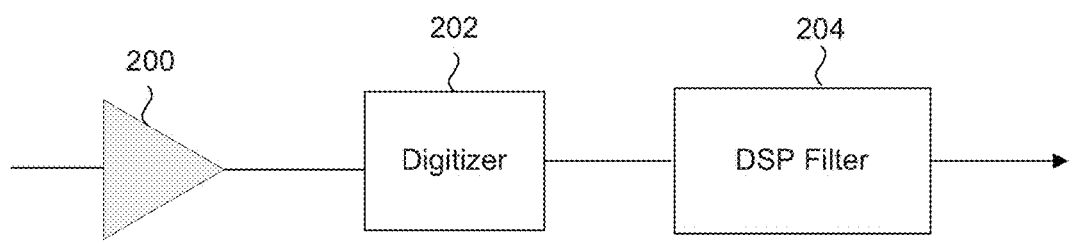
FIG. 2 illustrates the conventional oscilloscope architecture for acquiring a waveform.

This sort of system requires an architecture feature within a real time test and measurement instrument, such as an oscilloscope, that can process and apply filters to the acquired separated waveforms with different S-parameter characteristics. FIG. 2 shows a conventional oscilloscope architecture for acquiring a waveform and applying bandwidth correction filters. The acquired waveform is sent through an amplifier 200 and then to a digitizer 202. Then the digitized waveform or signal is sent to a DSP filter 204. In conventional oscilloscope architecture, there is inter-system interference. That is, a conventional DSP bandwidth filter may overlap regions that have different characteristics and therefore combine and smear the two system responses causing the inter-system interference.

Figure 3:
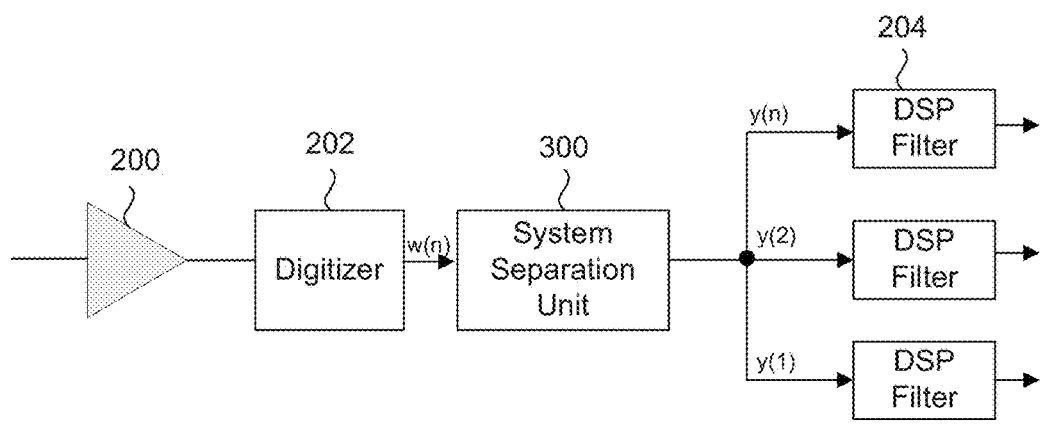
FIG. 3 illustrates an oscilloscope of the disclosed technology with a system separation unit.
Figure 4:
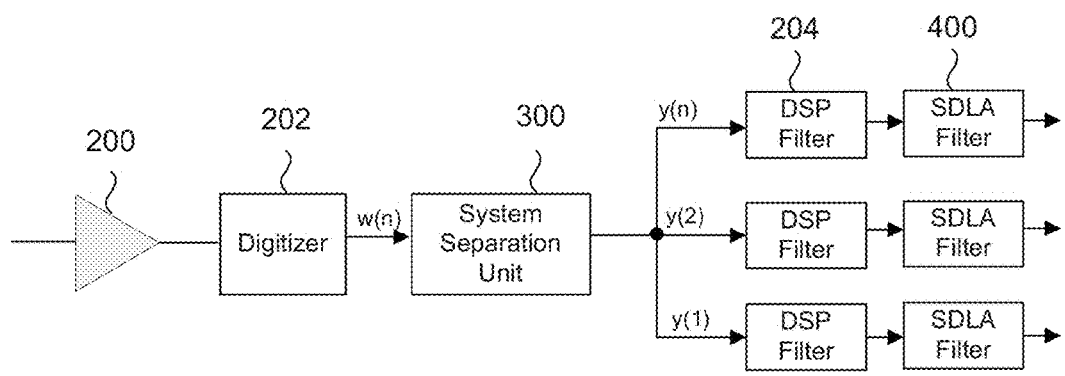
FIG. 4 illustrates an oscilloscope of the disclosed technology with additional SDLA filters that may be applied to the separated waveforms.

FIG. 3 shows one embodiment of the disclosed technology. The test and measurement instrument of FIG. 3 includes an amplifier 200 and a digitizer 202. As discussed above with respect to FIG. 2, the acquired waveform from a DUT is sent through the amplifier 200 and the digitizer 202 from a receiver (not shown). The receiver may be, for example, a probe to acquire the waveform from the DUT. The digitized waveform is then sent to a system separation unit 300, rather than directly to a DSP filter 204 as shown in FIG. 2. After the digitized waveform has been separated by the system separation unit 300, each of the separated sections of the waveform y(1) through y(n) are sent to DSP filters 204. The system-separated waveforms are represented by y(1), y(2), . . . y(n), where each index in the label represents a different S-parameter configuration of the DUT system parameters at some instance in the acquired waveform x(n). As seen in FIG. 4, the separated sections of the waveforms can also be sent to SDLA filters 400 after having been processed through the DSP filters 204.

DSP filters 204 are made up a combination of a number of filters that are combined and applied as one filter to the waveform. The DSP filter 204 may be made up of a bandwidth enhance filter that corrects for phase and magnitude errors of a scope channel, a probe filter (if a probe is used) that corrects phase and magnitude errors of the probe, a bandwidth limit filter selected by a user for reducing a bandwidth of the scope channel, and/or a temperature correction filter to compensate for changes in response due to temperature. The DSP filter 204 may be made up of any combination of these filters. The SDLA filters 400, on the other hand, are based on the S-parameters of the DUT, and the test and measurement system.

Although a single digitizer is described and shown, multiple digitizers can be used, as would be readily understood by one skilled in the art. The digitizer may consist of sample and hold circuits and a number of analog-to-digital converters that are interleaved.

The system separation unit 300 is capable of identifying the different portions of the waveform that are associated with the different characteristics of the waveform received from the DUT with different transmitters, as shown in FIG. 1, and as discussed in more detail below. That is, the system separation algorithm 300 processes the digitized waveform x(n) to locate and gate out the different portions of the waveform that are associated with different system S-parameter characteristics.

Initially, the system separation unit 300 determines what type of DUT the signals are being acquired from. The system separation unit 300 includes algorithms that will be switched in and configured depending on what type of system the waveforms are acquired from. The system separation unit 300 may identify the type of DUT by user input, which is discussed in more detail below.

Once the type of DUT has been determined, the different portions of the digitized waveform can be separated out. For example, a DUT with a MIPI bus can identify which transmitter is active in the acquired waveform at different time locations based on the different transmit speeds and different voltage levels. A DDR memory waveform, however, may require two waveform inputs to the system separation unit 300 in order to identify the different parts to separate. Alternatively, the system separation unit 300 may incorporate a correlation computation to identify and separate the different parts of the waveform. Finally, other systems may use strobes or events on a second waveform to identify the different portions of the acquired waveform.

In another embodiment, the system separation can be performed as shown in FIGS. 3 and 4 on the oscilloscope by turning off the oscilloscopes current DSP filters. Then, a Matlab math plugin is created to use in the scope math menu. The math plugin would perform the functions of the system separation unit discussed above and also apply the filters. However, a second separate math plugin may be required to obtain a second system separation. That is, one math plugin would yield one of the separated waveforms and the second math plugin would yield the second separate waveform.

Figure 5:
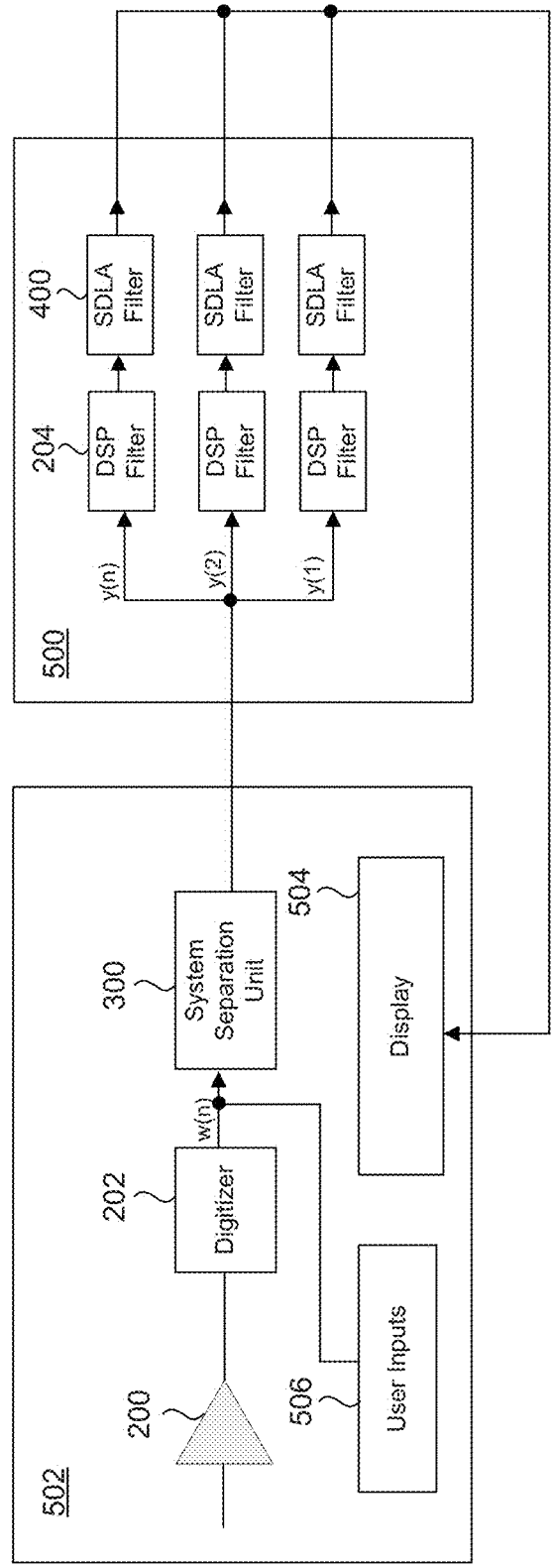
FIGS. 5 and 6 illustrates an oscilloscope and an external device for performing the system separation of the disclosed technology.
Figure 6:
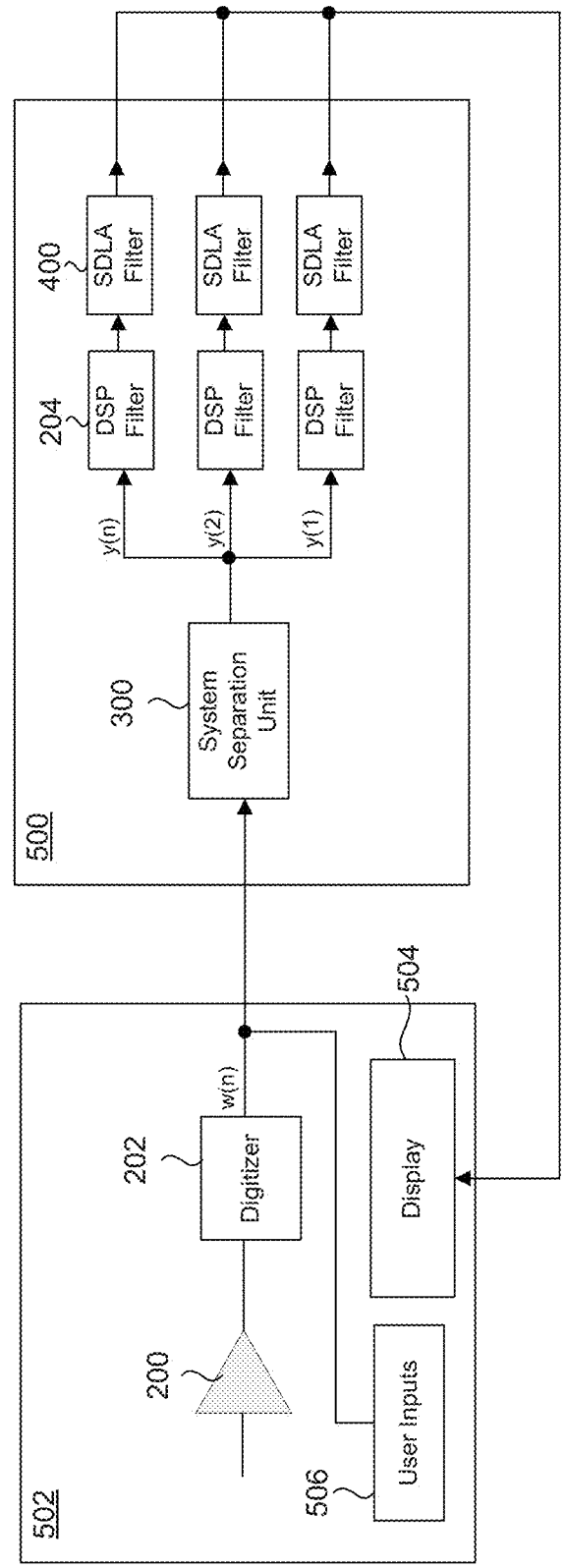

Alternative embodiments of the disclosed technology may involve the use of an external device 500 for part of the processing of the acquired waveform as shown in FIGS. 5 and 6. For example, in FIG. 5, the acquired waveform is received at the oscilloscope 502 and processed through the amplifier 200 and digitizer 202, as discussed above with respect to FIGS. 3 and 4. The digitized waveform is then sent to the system separation unit 300 to separate the digitized waveform as discussed above. The separated waveforms y(1), y(2), . . . y(n) are sent to an external component 500 for further processing. In the external component 500, the DSP filters 204 and the SDLA filters 400 may be applied. Then the processed signals are sent back to the oscilloscope for display to the user on the display 504 or to the memory of the oscilloscope (not shown).

Another alternative is shown in FIG. 6 in which the system separation unit 300 is also located on the external device 500 rather than on the oscilloscope 502. The embodiment of FIG. 6 can be implemented on oscilloscopes without having to modify the conventional configuration of oscilloscopes. This is done by first turning off the DSP filters on the oscilloscope 502. Then the waveform w(n) can be acquired and processed through the amplifier 200 and the digitizer 202, as discussed above. The digitized waveform w(n) is positioned in the external device 500. The DSP filters 204 would also be exported to the external device 500, as also shown in FIG. 5. The waveform is then processed through the system separation unit 300 in the external device 500. After the waveform has been separated, separated waveforms y(1), y(2), . . . y(n) are sent to DSP filters 204 and SDLA filters 400. Finally, the separated waveforms are imported back to the oscilloscope 502 for display on display 504 or to be stored in memory. In another embodiment, the external component 500 has a display to display the separated waveforms.

Figure 7:
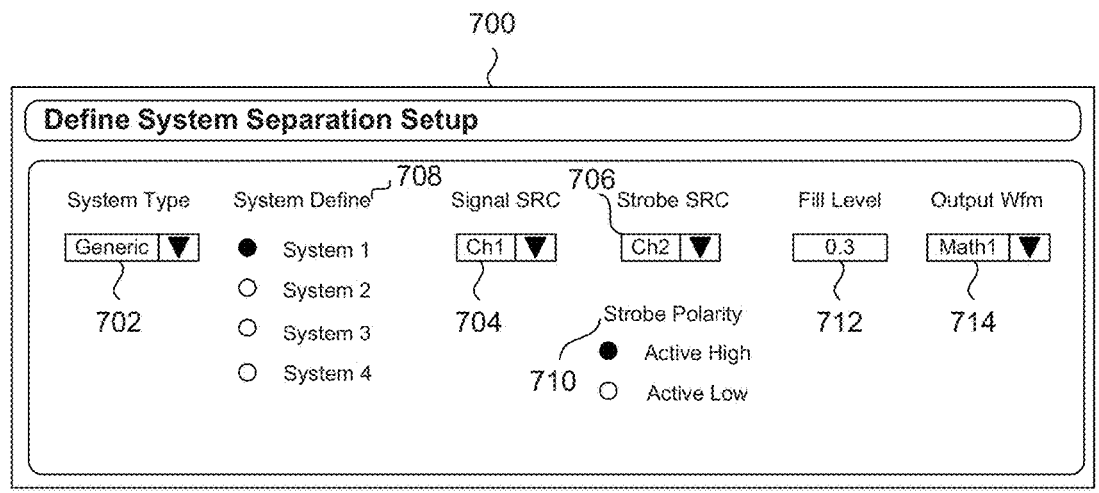
FIG. 7 illustrates a menu of the oscilloscope for performing the system separation of the disclosed technology.

The oscilloscope 502 includes a user input 506. The user input 506 may include a menu 700 shown on the display 504, as shown in FIG. 7. The menu 700 includes a selection list 702 of typical systems for which the oscilloscope 502 has custom separation algorithms. Since many systems have strobes or enable signals associated with regions where the S-parameters change, a more generic system separation algorithm that has a few basic parameters may also be incorporated in the menu 700.

The primary method of system separation that would apply to many different types of systems would incorporate the use of strobed gating. FIG. 7 shows a menu 700 with a generic system selected in the selection list 702 using strobed gating. A user would select the generic option in the selection list 702. Then, the signal source channel is selected from another selection list 704. The strobe source channel is also selected from a selection list 706. The duration of the strobe signal indicates the time interval for which the system has one set of S-parameters associated with a portion of the signal of interest. The menu 700 would also include a system define 708 to select which of four possible systems to separate, a reject fill level 712 to set the level of data that will replace gated out regions, and an output waveform selection 714. Although not shown, the menu 700 may also include a strobe polarity input to determine a correct gate region and a strobe threshold input to adjust the threshold level for the start of a gate.

When a generic system is selected in the menu 700, the user inputs the necessary data through the menu 700. Then, as the waveform is being acquired, at each region where the strobe waveform has an active pulse, that interval of the waveform is used to gate the corresponding desired waveform area into a new waveform. This is done by locating the gated area in the new waveform at the same time position it was in the old waveform and filling in the areas of the new waveform that have no signal from gating with a reject fill level value from the menu 700. If both the systems that are separated are to be analyzed, then a second waveform can be created continuing to use only gated regions from the second system. The device, however, is not limited to separating two systems only. More than two systems can be separated using the same procedures discussed above. Once the systems are separated, then the filters are provided as shown in one of FIGS. 3 through 6.

Rather than a generic system being selected in the selection list 702 in menu 700, a MIPI system may be selected. There are two possible methods to separate out different waveforms with different characteristics for a MIPI system.

The first method comprises using strobed gating, as discussed above with respect to the generic system. The region of interest can be separated out of the high-speed data transmission. This process would create a new waveform that contains only the gated regions. All of the regions that were eliminated by the gating would be filled with the high-speed common level so that the gated regions of interest maintain the correct time locations in the system-separated waveform.

The second method comprises an algorithm that looks at the waveform and detects the transitions that go to the high levels. The algorithm can identify the low power transmission areas by keeping each successive edge that went between low and high level associated with a low power transmission. These successive edges would be gated out up to the point where edges that match the high-speed transmission output start occurring. The high level low power transitions generate states that signal the beginning of high-speed transmissions. These states can also be used as part of this process.

Further, a DDR memory may be selected in the selection list 702 of the menu 700. If the DDR memory is selected, then the phase of the strobe signal can identify whether the operation is a read or write operation. The phase of the strobe signal may be used for identifying the region to gate from the waveform. However, a DDR system can also be separated by using a strobe signal as discussed above with respect to the generic system separator.

Although some of the above discussed embodiments discuss combining the separated waveforms back into a single waveform at correct time positions, the test and measurement instrument and/or external device are capable of maintaining the separated waveforms without fill levels inserted; rather, the fill areas would be discarded. That is, an array of waveforms are gated out for one DUT characteristic and another array of waveforms are gated out for a different DUT characteristic. Each of the arrays may be outputted and displayed to a user.

One or more aspects of the invention may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a non-transitory computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects of the invention, and such data structures are contemplated within the scope of computer executable instructions and computer-usable data described herein.

Having described and illustrated the principles of the disclosed technology in a preferred embodiment thereof, it should be apparent that the disclosed technology can be modified in arrangement and detail without departing from such principles. We claim all modifications and variations coming within the spirit and scope of the following claims.

What is claimed is:

1. A test and measurement instrument, comprising:
    a receiver structured to receive a waveform, from a device under test, that includes a first portion associated with first S-parameter characteristics of a first configuration of the device under test and a second portion associated with second S-parameter characteristics of a second configuration of the device under test;
    a digitizer structured to digitize the waveform;
    a processor configured to:
        identify the first portion of the digitized waveform based on the first S-parameter characteristics and the second portion of the digitized waveform based on the second S-parameter characteristics, and separate the first identified portion of the digitized waveform into a first waveform and the second identified portion of the digitized waveform into a second waveform; and a display to display the first and second waveforms to a user.

2. The test and measurement instrument of claim 1, further comprising a digital signal processing (DSP) filter, wherein to separate the first identified portion of the digitized waveform into the first waveform and the second identified portion of the digitized waveform into the second waveform is performed through application of the DSP filter to the first identified portion and the second identified portion separately.

3. The test and measurement instrument of claim 2, further comprising a serial data link analysis (SDLA) filter, wherein to separate the first identified portion of the digitized waveform into the first waveform and the second identified portion of the digitized waveform into the second waveform is performed through application of the SDLA filter after application of the DSP filter.

4. The test and measurement instrument of claim 1, wherein the processor is further configured to place the first and second waveforms into a single waveform and maintain the relative time position with a fill level between the first and second waveforms.

5. The test and measurement instrument of claim 1, further comprising a user input to receive a designation of type of device under test being tested.

6. A method of preventing inter-system interference while acquiring waveforms in a test and measurement instrument, comprising:
  receiving, by the test and measurement instrument, a waveform from a device under test, the waveform including a first portion associated with first S-parameter characteristics of a first configuration of the device under test and a second portion associated with second S-parameter characteristics of a second configuration of the device under test;
  digitizing the waveform to produce a digitized waveform;
  identifying the first portion of the digitized waveform based on the first S parameter characteristics and the second portion of the digitized waveform based on the second S-parameter characteristics;
  separating the first identified portion of the digitized waveform into a first waveform and the second identified portion of the digitized waveform into a second waveform; and
  displaying the first and second waveforms to a user.

7. The method of claim 6, further comprising applying a digital signal processing (DSP) filter to the first waveform to produce a first filtered waveform and the second waveform to produce a second filtered waveform.

8. The method of claim 7, further comprising applying a serial data link analysis (SDLA) filter to each of the first and second filtered waveforms.

9. The method of claim 6, further comprising combining the first and second waveforms into a single waveform while maintaining the relative time position with a fill level between the first and second waveforms.

10. The method of claim 6, further comprising receiving a user input to designate type of device under test being tested.

11. The method of claim 6, wherein the receiving step and the digitizing step are performed on a test and measurement instrument.

12. The method of claim 11, wherein the identifying step and the separating step are performed on an external device and exported to the test and measurement instrument for display.

13. The method of claim 11, wherein the identifying step and the separating step are also performed on the test and measurement instrument.

14. The method of claim 12, further comprising:
  applying a digital signal processing (DSP) filter to each of the first and second waveforms to produce first and second filtered waveforms; and
  applying a serial data link analysis (SDLA) filter to the first and second filtered waveforms.

15. A test and measurement instrument, comprising:
  means for receiving a waveform from a device under test, the waveform including a first portion associated with first S-parameter characteristics of a first configuration of the device under test and a second portion associated with second S-parameter characteristics of a second configuration of the device under test;
  means for digitizing the waveform to produce a digitized waveform;
  means for identifying the first portion of the digitized waveform based on the first S parameter characteristics and the second portion of the digitized waveform based on the second S-parameter characteristics;
  means for separating the first identified portion of the digitized waveform into a first waveform and the second identified portion of the digitized waveform into a second waveform; and
  means for displaying the first and second waveforms to a user.

16. A non-transitory computer readable medium having stored thereon a computer program for execution by a processor of a test and measurement instrument to perform a method as claimed in claim 6.

* * * * *